(12) United States Patent
Moriyama et al.

(10) Patent No.: US 8,423,166 B2
(45) Date of Patent: Apr. 16, 2013

(54) METHOD FOR CALCULATING GRINDING PORTION OF PRE-GRINDING DENTURE

(75) Inventors: Takeshi Moriyama, Kyoto (JP); Yusei Kadobayashi, Kyoto (JP)

(73) Assignee: Kabushiki Kaisha Shofu, Kyoto (JP)

( * ) Notice: Subject to any disclaimer, the term of this patent is extended or adjusted under 35 U.S.C. 154(b) by 61 days.

(21) Appl. No.: 13/168,213

(22) Filed: Jun. 24, 2011

(65) Prior Publication Data

US 2012/0015321 A1    Jan. 19, 2012

(30) Foreign Application Priority Data

Jun. 25, 2010   (JP) ................................ 2010-145274

(51) Int. Cl.
*G06F 19/00* (2011.01)

(52) U.S. Cl.
USPC .................... 700/97; 433/68; 433/69; 433/70

(58) Field of Classification Search .................... 700/97; 433/68–70
See application file for complete search history.

(56) References Cited

U.S. PATENT DOCUMENTS

| | | | | |
|---|---|---|---|---|
| 4,264,308 | A * | 4/1981 | Tanaka ........................... | 433/223 |
| 4,981,437 | A * | 1/1991 | Wilcox ........................... | 433/55 |
| 5,587,912 | A | 12/1996 | Andersson et al. | |
| 7,806,687 | B2 | 10/2010 | Minagi et al. | |
| 2008/0038695 | A1 | 2/2008 | Carlson | |
| 2008/0311537 | A1 | 12/2008 | Minagi et al. | |
| 2009/0155738 | A1* | 6/2009 | Shindo et al. .................... | 433/68 |
| 2009/0191509 | A1* | 7/2009 | Zudorf et al. .................... | 433/213 |
| 2011/0318703 | A1* | 12/2011 | Moriyama et al. .............. | 433/69 |
| 2011/0318709 | A1* | 12/2011 | Moriyama et al. ............. | 433/191 |
| 2012/0003604 | A1* | 1/2012 | Moriyama et al. .............. | 433/71 |

FOREIGN PATENT DOCUMENTS

| | | |
|---|---|---|
| EP | 0 375 982 | 7/1990 |
| JP | 5-95968 | 4/1993 |
| JP | 7-152822 | 6/1995 |
| JP | 10-225469 | 8/1998 |
| JP | 2000-316876 | 11/2000 |

(Continued)

OTHER PUBLICATIONS

"A Method for correction of increased vertical dimension in complete dentures", D.U. Kharat, The Saudi Dental Journal, vol. 1, No. 3, 1990.*

(Continued)

*Primary Examiner* — Michael D Masinick
(74) *Attorney, Agent, or Firm* — Wenderoth, Lind & Ponack, L.L.P.

(57) ABSTRACT

A jaw-relation reproduction condition is determined by measuring a jaw movement of a patient, and reproducing a jaw state of the patient on an occlusion-state reproducing apparatus in accordance with the jaw-relation reproduction condition. Dentures are arranged on the apparatus in accordance with the jaw-relation reproduction condition to prepare pre-grinding dentures. Denture data with reference points which is three-dimensional image data containing reference points that represents a positional relationship between the jaw-relation reproduction condition and the dentures and an occlusal surface of the dentures. An occlusion state of the denture data with the reference points is reproduced by using the jaw-relation reproduction condition on a three-dimensional image. Grinding data of a grinding portion is determined under a dynamic condition or set condition from a portion surrounded by an image of upper and lower jaws on the three dimensional image in a reproduced occlusal state.

10 Claims, 4 Drawing Sheets

FOREIGN PATENT DOCUMENTS

| | | |
|---|---|---|
| JP | 2001-517480 | 10/2001 |
| JP | 2003-99486 | 4/2003 |
| JP | 2006-520229 | 9/2006 |
| JP | 2007/021007 | 2/2007 |
| JP | 2010-17467 | 1/2010 |
| WO | 99/15100 | 4/1999 |
| WO | 2004/082512 | 9/2004 |

OTHER PUBLICATIONS

Extended European Search Report (in English language) issued Dec. 4, 2012 in corresponding European patent application No. 11 00 5212.

* cited by examiner

METHOD FOR CALCULATING GRINDING PORTION OF PRE-GRINDING DENTURE

BACKGROUND OF THE INVENTION (1) Field of the Invention

This invention relates to a method of grinding denture, a program for calculating grinding portion of pre-grinding denture, an occlusal condition reconstructing Device, a denture data measuring Equipment, a denture grinding machine, an artificial tooth for automated grinding, a method for determining occlusal adjustment portion and program thereof, and a Program for indicating condition of contact portion of denture.

(2) Description of Related Art

Heretofore, after making dentures, the dentures have been adjusted by rubbing the maxillary denture and the mandibular denture against each other in a process called the grinding. The grinding has been performed as a process including two steps of: adjusting the dentures by attaching the dentures on an articulator and grinding little by little with a grinder while ascertaining contact portions between the maxillary denture and the mandibular denture; and then adjusting the dentures by applying a paste material containing abrasive particles to the occlusal surface and rubbing the maxillary denture and the mandibular denture against each other. Depending on the conditions of the dentures, the adjustment of the dentures has been performed using only one of these steps in some cases. However, there is no way to know whether portions to be ground are correctly determined. Thus, it has been difficult to determine whether the grinding is performed correctly.

Furthermore, it is necessary to perform grinding or an occlusal adjustment of the prepared prosthesis when the antagonist is a natural tooth. The occlusal adjustment of the prosthesis is adjusted by grinding the prosthesis little by little with a grinder to perform polish finishing while ascertaining contact portions of the prosthesis. However, there is also no way to know whether the portions to be occlusal adjusted was correctly determined, and it was also difficult to determine whether the occlusal adjustment was performed correctly.

Furthermore, dental students are educated about grinding and occlusal adjustment of prostheses at their universities. Although the teachers of each university carefully teach the grinding sites of prostheses and the occlusal adjustment thereof, a lot of times have been required for improving the skills of the students because of difficulty in these works. Students have a narrow window of opportunity to learn from one another a method of clearly recognizing a difference between the properly performed condition of grinding or occlusal adjustment and the improperly performed condition in an objective manner. In addition, they are difficult in knowing their acquisition degrees of the skills. The students have to ask a dentistry instructor to confirm whether the grinding and occlusal adjustment steps are performed properly. There has been no way to know how to personally determine the grinding and occlusal adjustment in an objective manner.

JP-A-05-95968 discloses a dental model processing apparatus which is capable of drilling work for inserting a pin on a bottom surface of a dental model on an upper work table and also capable of grinding inner and outer profile surfaces of the dental model on a lower work table. This processing apparatus does not intend for grinding an occlusal surface. Thus, it cannot be used for grinding the occlusal surface because of its structure.

JP-A-10-225469 discloses a method of arranging artificial teeth in which ground artificial tooth are used. However, a grinding adjustment is required because a small distortion or the like occurs in the production of a denture base. Thus, JP-A-10-225469 is not relevant to the present invention.

JP-A-2000-316876 discloses a drive apparatus for artificial-tooth grinding that intends to enhance an efficiency of grinding artificial tooth on an articulator. In the drive apparatus, a transducer linked to an oscillator circuit is installed as a driving unit for grinding on an articulator for grinding and occlusal adjustment of artificial tooth. However, the drive apparatus performs the grinding by rubbing the maxillary denture and the mandibular denture against each other. Thus, it is difficult to perform arbitrary adjustment.

Prior Art Document

JP-A-05-95968
JP-A-10-225469
JP-A-2000-316876

SUMMARY OF THE INVENTION

Conventionally, maxillomandibular grinding is a work operation performed by an experienced technician. In this grinding work, contact portions of the occlusal surface are determined and grinding thereof are performed little by little and repeated so as not to grind too much. However, it is the most difficult work to adjust a plurality of faces on the occlusal surface until the faces are rubbed. Although the experienced technician has been reproduced easily, less skilled persons had taken a lot of trouble over reproduction.

Completely adjusting the contact portions of the occlusal surface is difficult even for the experience technician and takes one hour or more.

Artificial tooth which are portions where the upper and lower jaws come into contact with each other has an indeterminate form. Thus, the portions where the upper and lower jaws come into contact with each other are hardly ascertained. It has been difficult to clearly determine the contact position. An occlusal contact state is ascertained by sandwiching an articulating paper between the upper jaw and the lower jaw. A measurement error may occur due to the thickness of the articulating paper. Since only the contact portions of the articulating paper are stained, information about where the stained portion corresponds to the portion of the occlusal surface and about whether the contact is a dynamic contact or a static contact is not obtained.

In the occlusal adjustment, it has been necessary to select a method that does not damage natural tooth by adjusting the artificial teeth along the profiles of the natural tooth.

The maxillomandibular grinding may be realized by grinding the artificial teeth little by little as the maxillomandibular contact state is confirmed by sandwiching the articulating paper between the upper jaw and the lower jaw. It is adjusted by increasing the contact faces between the upper jaw and the lower jaw. The contact portions of the articulating paper form holes. Even if they are not in contact, when the upper jaw and the low jaw are brought into close proximity with each other to a distance smaller than the thickness of the articulating paper, the articulating paper is compressed and thinned. The degree of thinness can be confirmed by optical penetration and the amount of gap can be confirmed by the transmission amount of light. As illustrated in FIG. 1, in order to bring each tooth in contact with the corresponding tooth, grinding is advanced with reference to the thickness of articulating paper while the contact portion between the upper jaw and the lower jaw is confirmed with the articulating paper.

Naturally, only the articulating paper can be relied under the conditions that the upper and law jaws moves freely on the articulator and it is hardly determined how far the contact areas thereof slide. Thus, an advanced technology has been required.

The object of the present invention is to provide a method for grinding a dental denture, a method for occlusal adjustment and a program thereof, and programs for confirming grinding and occlusal adjustment, and acceptance where the grinding portion of a denture can be determined simply and quickly, and grinding can be performed on such a portion easily; dental students can ascertain whether grinding or occlusal adjustment, which are uniquely performed by them, are endurable in medical treatment, and useful in confirmation test and acceptance-line selection.

In order to overcome the above circumstances, a first aspect of the present invention is a method for grinding a denture in denture production, the denture grinding method comprising:

(1) a jaw-relation reproduction step of determining a jaw-relation reproduction condition by measuring a jaw movement of a patient, and reproducing a jaw state of the patient on an occlusion-state reproducing apparatus in accordance with the jaw-relation reproduction condition;

(2) a pre-grinding denture production step of arranging dentures on the occlusion-state reproducing apparatus in accordance with the jaw-relation reproduction condition and preparing pre-grinding dentures;

(3) a measurement step for denture data with reference points of measuring denture data with reference points which is three-dimensional image data containing reference points that represents a positional relationship between the jaw-relation reproduction condition and the dentures and an occlusal surface of the dentures;

(4) an occlusion-state reproduction step of reproducing an occlusion state of the denture data with reference points by using the jaw-relation reproduction condition on a three-dimensional image;

(5) a grinding data determination step of determining grinding data of grinding portions under a dynamic condition or set condition from a portion surrounded by an image of upper and lower jaws on the three dimensional image in a reproduced occlusal state;

(6) a preparation step for denture data with reference points having grinding data for preparing denture data with reference points having grinding data, where the denture data with reference points is additionally provided with the grinding data; and (7) a grinding step for pre-grinding dentures, which grinds the pre-grinding denture based on the denture data with reference points having grinding data.

The condition may be selected from a static condition and a dynamic condition.

Another aspect of the present invention is a dental program for calculating a grinding portion of a pre-grinding denture. The program allows a computer to execute:

a data input step of inputting a maxillomandibular jaw-relation reproduction condition and denture data with reference points having reference points representing a positional relationship between the jaw-relation reproduction condition and an upper jaw and a lower jaw;

a determination step for a position of maxillomandibular denture data with reference points of reproducing an occlusion state of the input denture data with the reference points by using the jaw-relation reproduction condition on a three-dimensional image, and determining a positional relationship of the denture data with reference points of the upper and lower jaws;

a grinding portion determination step of determining a portion surrounded by an image of upper jaws and lower jaws on the three-dimensional image in a reproduced occlusion state; and a grinding data calculation step of calculating grinding data of a grinding portion under a dynamic condition or set condition from the portion surrounded by the image of the upper and lower jaws.

Another aspect of the present invention is an occlusion-state reproducing apparatus used for a denture grinding method, the apparatus including:

an articulator having an upper arch that corresponds to an upper jaw of a patient and a lower arch that corresponds to a lower arch of the patient; and reference points on the upper arches and the lower arches.

Furthermore, other aspects of the present invention include: reference points denture data measurement apparatus used for the denture grinding method, and a dental occlusal grinding apparatus for grinding a denture, in which a processing NC program is created by using grinding data calculated by a dental program for calculating a grinding portion of a pre-grinding denture.

Another aspect of the present invention is an artificial tooth for automatic grinding, used as a denture in a denture grinding method, where a food-flowing groove of 0.5 to 3.0 mm is provided between a protrusive occlusal facet and a posterior occlusal facet that are present between cusps of the adjacent artificial teeth.

The above inventive grinding may be generally used in the occlusal adjustment. A method for performing occlusal adjustment in the denture production includes:

(1) a jaw-relation reproduction step of determining a jaw-relation reproduction condition by measuring a jaw movement of a patient, and reproducing a jaw state of the patient on an occlusion-state reproducing apparatus in accordance with the jaw-relation reproduction condition;

(2) a pre-occlusal adjustment denture production step of arranging dentures on the occlusion-state reproducing apparatus in accordance with the jaw-relation reproduction condition and preparing pre-occlusal adjustment dentures;

(3) a measurement step for denture data with reference points of measuring denture data with reference points which is three-dimensional image data containing reference points that represent a positional relationship between the jaw-relation reproduction condition and the dentures and an occlusal surface of the dentures;

(4) an occlusion-state reproduction step of reproducing an occlusion state of the denture data with reference points by using the jaw-relation reproduction condition on a three-dimensional image;

(5) an occlusal adjustment data determination step of determining occlusal adjustment data under a dynamic condition or set condition from a portion surrounded by an image of upper and lower jaws on the three dimensional image in a reproduced occlusion-state; and (6) a preparation step for denture data with reference points having occlusal adjustment data for preparing denture data with reference points having occlusal adjustment data, where denture data with reference points is provided with occlusal adjustment data.

The condition may be selected from a static condition and a dynamic condition.

Another aspect of the present invention is a method for determining an occlusal adjustment portion of a dental prosthesis by using a computer 3-D data, where the 3D-data includes rubbing natural teeth data in upper and lower jaws, prosthesis data and the natural teeth data corresponding thereto, the method including:

(A) an identification step for rubbing natural teeth data portion in upper and lower jaws for identifying a rubbing natural teeth data portion in the upper and lower jaws in maxillomandibular 3D-data;

(B) an identification step for smooth sliding of natural teeth portion face data for identifying so that the rubbing natural teeth data portion in the upper and raw jaws and the prosthesis data are laid on each other and the prosthesis data is smoothly slid on the rubbing natural teeth data portion in the upper and raw jaws; and (C) a determination step for an occlusal adjustment portion of determining an occlusal adjustment portion by moving maxillomandibular 3D-data along with at least one face data of rubbing natural teeth portion and remaining a trace of a region surrounded by 3D-data on the side of prosthesis data to determine a region surrounded by the 3D-data as an occlusal adjustment portion.

Another aspect of the present invention is a program for determining an occlusal adjustment portion of a dental prosthesis by using a computer 3-D data, where the 3D-data includes rubbing natural teeth data in upper and lower jaws, prosthesis data and the natural teeth data corresponding thereto, the program allowing a computer to execute:

(A) an identification step for rubbing natural teeth data portion in upper and lower jaws for identifying a rubbing natural teeth data portion in the upper and lower jaws in maxillomandibular 3D-data;

(B) an identification step for smooth sliding of natural teeth portion face data for identifying so that the rubbing natural teeth data portion in the upper and raw jaws and the prosthesis data are laid on each other and the prosthesis data is smoothly slid on the rubbing natural teeth data portion in the upper and raw jaws; and (C) a determination step for an occlusal adjustment portion of determining an occlusal adjustment portion by moving maxillomandibular 3D-data along with at least one face data of rubbing natural teeth portion and remaining a trace of a region surrounded by 3D-data on the side of prosthesis data to determine a region surrounded by the 3D-data as an occlusal adjustment portion.

Another aspect of the present invention is a dental program for representing state of a contact portion, which represents the state of a contact portion between an upper jaw and a lower jaw, the program allowing a computer to execute:

a data input step of inputting maxillomandibular data;

a determination step for a position of maxillomandibular data position of reproducing an occlusal state of the maxillomandibular data and determining a position of the maxillomandibular data; and a display step for state of contact position of maxillomandibular data of displaying a portion having a specific opposing jaw data in a specific approximate region of the maxillomandibular data.

Another aspect of the present invention is a dental program for representing state of a contact portion, which represents the state of a contact portion between an upper jaw and a lower jaw, where the data input step is for inputting a maxillomandibular jaw-relation reproduction condition, and maxillomandibular denture data with reference points that represent a positional relation between the maxillomandibular jaw-relation reproduction condition and upper jaw and a lower jaw; and the determination step for the maxillomandibular data position is for determining a positional relationship between the upper jaw and the lower jaw by using reference points in accordance with the jaw-relation reproduction condition of input data.

EFFECTS OF THE INVENTION

The conventional occlusal adjustment requires a lot of skill. The occlusal adjustment has been performed by determining contact portions of occlusal surfaces between upper and lower jaws and repeating grinding thereof little by little so as not to grind too much.

There is a style called "full balanced occlusion" where all teeth slid and come into contact with the corresponding tooth when moving in any direction (clenching). This is requires an adjustment to be performed until a plurality of faces in the occlusal surface become rubbing. However, such adjustment has been the most difficult work even for experienced technician and needed labors to reproduce the full balanced occlusion.

Even if it was performed by an experienced technician, it has been difficult to completely match the contact portions of the occlusal surfaces and sometimes more than one hour has been taken.

According to the present invention, it is possible to reproduce the "full balanced occlusion" easily even without being performed by an experienced technician.

Thus, dentures with constant occlusal adjustment can be produced without difference between technicians.

Artificial teeth where the upper and lower jaws come into contact with each other have an infinite shape. Thus, in the conventional method using carbonic paper, it has been very difficult to find contact portions between the upper and lower jaws and clearly define the contact positions.

An occlusal contact state has been ascertained by sandwiching an articulating paper between the upper jaw and the lower jaw. However, the contact portions have been hardly found because an error of measurement by the thickness of articulating paper arised, only the contact portion was marked, and a correspondence relationship between marked portions was unclear. Furthermore, the occlusal adjustment has been required under not only a static contact condition but also a dynamic contact condition. In this case, further skills have been required. In contrast, according to the present invention, the occlusal adjustment can be performed easily.

In the case of occlusal adjustment where a natural tooth remains, the occlusal adjustment can be easily performed while considering the profile of the natural tooth without damaging the natural tooth.

As an application of the present invention, a dental student may be allowed to confirm whether occlusal adjustment personally performed by the student is correctly carried out as a medical treatment.

According to the present invention, even an operator is not an experienced technician, the ideal relationship between the upper and lower jaws can be reproduced in the denture. Since the present invention may execute grinding with CAM, any operators may be prevented from being injured with cutting chips or the like and inhaling dust. Thus, the operator can work without concerning his or her health. Conventionally, furthermore, especially in the case of using such as dental porcelain, grinding has been very hard work because it is very hard material and thus technicians have been suffering troubles. In contrast, according to the present invention, it is possible to proceed grinding of dental porcelain easily.

DETAILED DESCRIPTION OF PREFERRED EMBODIMENTS

Figure 1:
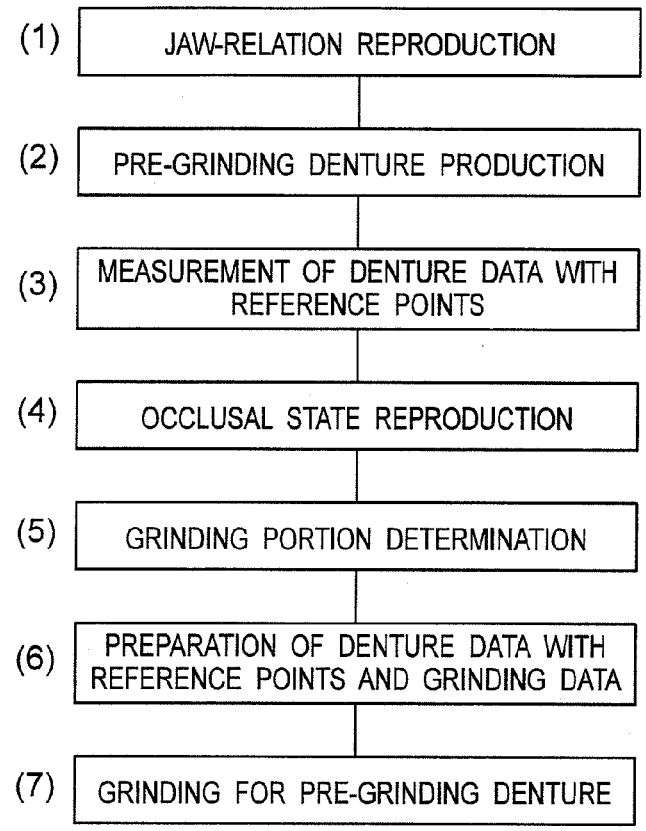
FIG. 1 is a flowchart illustrating a denture-grinding method according to the present invention.

The present invention include a method for performing grinding in denture production, a method for adjusting denture occlusion, and programs for executing these methods. The programs of the invention are employed for determining grinding portions of a denture, and grinding an undesired portion of an occlusal surface by using CAD/CAM.

A typical process for producing a denture is as follows:

1. An intraoral form of a patient is taken to prepare an impression.
2. An intraoral model of the patient is made of plaster using the impression and a constituent resin base plate is prepared on the model.
3. Wax is poured into a mold form and fixed in the shape of an arch. The wax is then mounted on the base plate to form a wax rim on which artificial tooth are arranged. A combination of this wax rim and the base plate is referred to as a bite plate.
4. The bite plate is applied to a patient to take a bite form of the patient.
5. Maxillary and mandibular models equipped with the bite plate is attached to an articulator to reproduce an occlusion state on the articulator.
6. Artificial tooth suitable for the patient are selected and maxillary anterior artificial teeth are arranged first on the maxillary wax rim and then mandibular anterior artificial teeth on the mandibular wax rim.
7. The maxillary height is slightly increased by adjusting an incisal pole of the articulator and mandible and maxillary molar artificial teeth are then arranged on the wax rim.
8. The incisal pole of the articulator is returned to the original state and an occlusal adjustment for grinding high portions is performed. In the occlusal adjustment, an articulating paper is sandwiched between the upper jaw and the lower jaw and a portion that strongly comes into contact with the opposite portion is ground.
9. A cervix (neck portion) state and a gingival regional state of the anterior teeth are reproduced.
10. The denture model with artificial teeth arranged on the bite plate is applied to the buccal cavity of the patient on a trial basis and information about required correction is then obtained.
11. Portions which should be corrected are corrected according to the information.
12. The denture model is separated in a flask (frame) and embedded in plaster and solidified.
13. The flask is heated to soften the wax of the denture model and the flask is removed to melt the wax, resulting in a mold.
14. A separation material is applied to the plaster portion of the mold and resin for denture plate (synthetic resin)) is then poured into the mold. The upper and lower mold forms are combined together and then pressed by a press.
15. Excessive resin is removed and the upper and lower frames are set, followed by being subjected to heat to harden the resin.
16. The mold forms are removed and the plaster is then taken out to scrape out the denture.
17. The denture is attached to the articulator again and occlusal imbalance caused by contraction occurred in resin hardening is then corrected. Articulating paper is used in occlusal correction.
18. Occlusion when the jaw is moved back and forth and left and right is adjusted with an articulating paper (this adjustment is a last occlusal adjustment and called grinding).
19. Removing burrs from the resin, polishing is performed.

In the step of producing a denture, the intraoral form is taken, the wax rim is formed, the artificial teeth are arranged, and the wax is replaced with the resin by a lost-wax process. In this case, the contraction of the resin causes a positional displacement of artificial teeth and interference occurs when the artificial teeth are bitten as dentures by the upper and lower jaws. The grinding is the adjustment of such an interference portion. Even if the occlusion is correctly performed on the dentures, the grinding may be performed to change the occlusal relationship depending on the status of the buccal cavity of the patient. The adjustment is performed in corporation with the movement of the jaws of the patient. According to the present invention, a series of these operations is performed using a program.

Here, in the case of a denture-grinding method, full dentures are preferable. Alternatively, partial dentures may be also used even in the case where the upper and lower jaws are a combination of dentures.

1. Denture Grinding Method

The denture-grinding method of the present invention includes the following processes as illustrated in FIG. 1.

(1) Jaw-relation reproduction step
(2) Pre-grinding denture production step
(3) Measurement step for denture data with reference points
(4) Occlusal state reproduction step
(5) Grinding portion determination step
(6) Preparation step for denture data with reference points having grinding data
(7) Grinding step for pre-grinding dentures (1) The jaw-relation reproduction step in which the jaw-relation reproduction conditions that can reproduce the conditions of the jaws of the patient are determined to reproduce the jaw relation will be described.

The jaw-relation reproduction step reproduces a positional relationship between the upper and lower jaws of the patient before the production of dentures. Usually, by using an articulator, the maxillomandibular movement is reproduced on the articulator by adjusting the movement of the condyle path of the articulator and incisal movement in corporation with the movement of the jaws.

It is necessary to decide moving directions that assume masticatory motion and opening/closing movement from the maxillomandibular centric occlusal position.

The conditions of the jaws of the patient include static conditions and dynamic conditions. Typically, the conditions include the position of the centric occlusal position and the directions of protrusive movement and lateral movement, and sometimes the direction of hinge movement.

These occlusal conditions can be reproduced by an occlusion-state reproducing apparatus, typically an articulator. The articulator can reproduce static relations and dynamic relations exactly.

The jaw-relation reproduction conditions include a sagittal condylar inclination, a balancing-side lateral condyle path, a regulatory mechanism of immediate side-shift, and a regulatory mechanism for an angle of lateral condyle path on the working side. Examples of the incisal path regulatory mechanism include a sagittal incisal path inclination and a lateral incisal path guide angle.

The method using the approximate values of the jaw movement in connection with the conditions of the patient is common. For example, the standard condylar distance is 110 mm, the distance between upper and lower arch is 110 mm, the maximum mandibular movement angle is 120 degrees, the inclination of sagittal condylar path is 30 degrees, and the angle of lateral condyle path is 15 degrees.

An important point is that it becomes clear how the upper jaw moves with respect to the lower jaw when the lower jaw is shifted from the centric occlusal position to the lateral movement.

As the simplest method, it is also possible to set the jaws so that the upper jaw slides forward at an angle of 10 degrees from the centric position in parallel to the lower jaw and the upper jaw further slides in the upper direction at an angle of 20 decrees with respect to the occlusal surface from the centric occlusal position.

In recent years, a method for directly reproducing a jaw movement has been investigated and a jaw-movement measurement apparatus has been developed. The jaw movement may be directly acquired by a jaw-movement measurement apparatus so that the jaw movement may be reproduced by a jaw-movement reproducing apparatus.

(2) The pre-grinding denture production step of producing a pre-grinding denture will be described. Here, dentures are produced according to the jaw-relation reproduction conditions of the occlusion-state reproducing apparatus to produce pre-grinding dentures before the step of grinding.

The pre-grinding denture production step is a step of producing dentures according to the maxillomandibular relation obtained in the above occlusion-state reproduction step. In other words, the pre-grinding denture production step is a step of producing a normal denture (steps 6 and 7 in the above denture production process). In the typical process, a wax rim is formed, artificial teeth are arranged along the wax rim and a pre-grinding denture is prepared by a lost wax process. Here, the production method is not particularly limited but the pre-grinding denture can be produced by any typical procedure.

The pre-grinding denture is not ground, so that it cannot be correctly occluded on the occlusion-state reproducing apparatus yet. In order to carry out correct occlusion on the occlusion-state reproducing apparatus, the grinding of the occlusal surface is performed according to the present invention.

(3) The step for measuring denture data with reference points by a denture data measurement apparatus will be described. Here, the denture data measurement apparatus measures the denture data with reference points, comprising three-dimensional image data of the occlusal surface of the denture and reference points representing a positional relation between the occlusion-state reproducing apparatus and the denture.

In this step, the position of the pre-grinding denture in the occlusion-state reproducing apparatus is measured so that an occlusion state can be reproduced in a computer in addition to obtaining the 3D-data of the produced pre-grinding denture. By setting up the maxillomandibular relation of the occlusion-state reproducing apparatus in advance, the occlusion state can be reproduced.

At least three reference points are required for the respective upper and lower arches of the reproducing device. Alternatively, three sides may be used. One side and one point are preferable. Specifically, it may be configured of three needle-like form or spherical surface (preferably globular shape) or may be a combination of a straight side and spherical surface of the reproducing device. Here, the 3D-data is necessary to have reference points for correctly calculating the maxillomandibular relation to be reproduced on a computer. A spherical surface is preferable in order to match the 3D-data on a computer.

Figure 2:
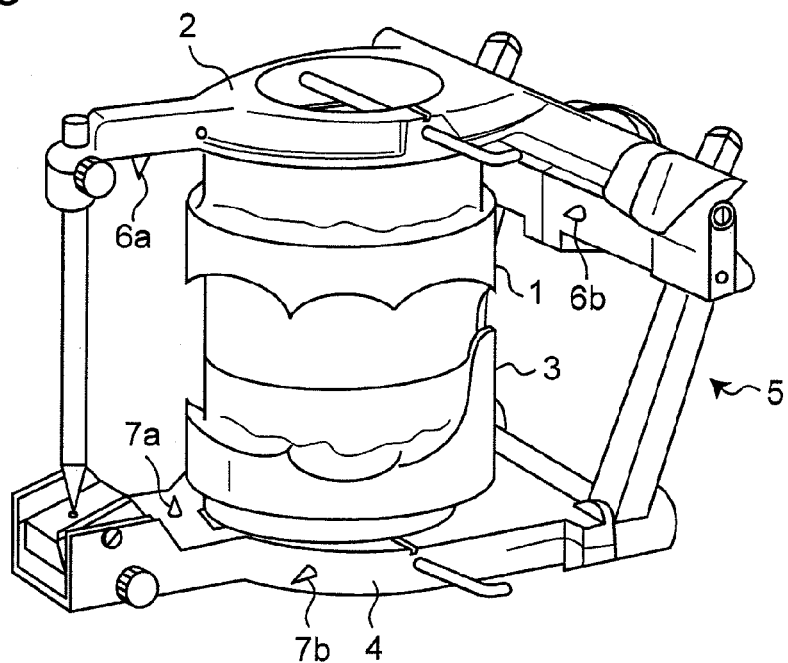
FIG. 2 is a perspective diagram illustrating a state where a maxillomandibular model is attached to an articulator having reference points.

The occlusion-state reproducing apparatus that determines the jaw-relation reproduction condition used for a denture grinding method is an articulator 5 having an upper arch 2 on which an upper jaw model 1 is attached and a lower arch 4 on which a lower jaw model 3 is attached. Preferably, as illustrated in FIG. 2, reference points 6a, 6b, and 6c and reference points 7a, 7b, and 7c are provided on the upper arch 2 and the lower arch 4, respectively.

(4) The occlusion-state reproduction step, which reproduces the occlusion state of the denture data with reference points by using the jaw-relation reproduction conditions, will be described.

In this step, an occlusion state is reproduced on a computer. The maxillomandibular relation of the occlusion-state reproducing apparatus can be arbitrarily configured on the computer.

Here, the positional relationship between the upper and lower jaws can be correctly simulated in the space of the computer. In the computer, the static relationship between the upper jaw and the lower jaw is represented. This relationship includes the reference points which are used for acquiring 3D-data. In the space of the computer, the movements of upper and lower jaws are simulated so that the 3D-data of the upper and lower jaws represents a static relation.

Preferably, the mandibular orthogonal coordinate system of the lower jaw and the orthogonal coordinate system of the upper jaw are configured. To reproduce the maxillomandibular occlusal state, from an arbitrary positional relationship between the upper and lower jaws, a direction along which the orthogonal coordinate system of the upper jaw moves with respect to the orthogonal coordinate system of the lower jaw may be arbitrarily calculated.

Figure 3:
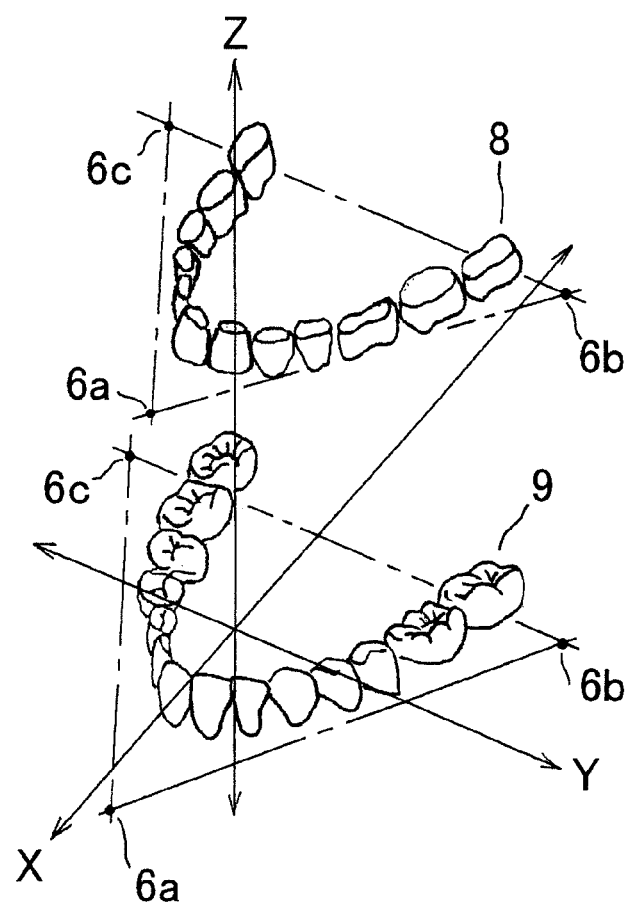
FIG. 3 is a diagram representing three-dimensional data of maxillomandibular occlusal surfaces on a three-dimensional space.

As illustrated in FIG. 3, the reference points on the orthogonal coordinate system of the lower jaw and the reference points on the orthogonal coordinate system of the upper jaw are preferably coincided with the reference points on the computer to reproduce the relationship between the movement of the denture data 8 of the upper jaw and the denture data 9 of the lower jaw.

In each orthogonal coordinate system, the positions of reference points are defined and aligned with the denture data obtained in the step of measuring the denture data.

Figure 4:
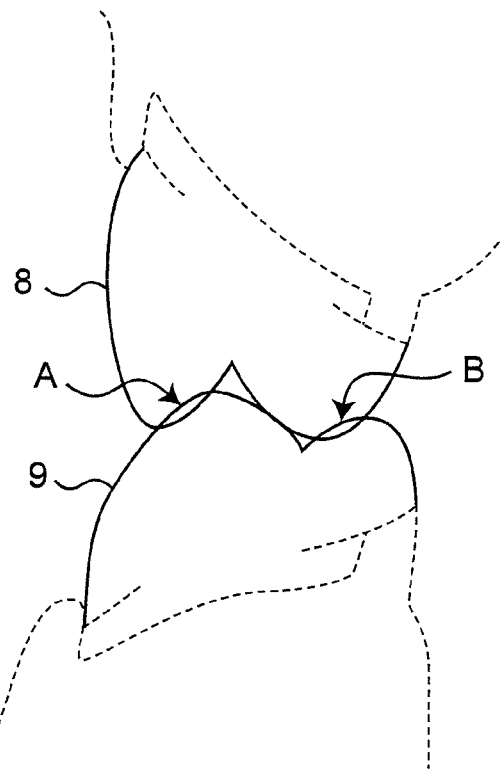
FIG. 4 is a diagram illustrating an occlusion state of the three-dimensional data of the axillomandibular occlusal surfaces.

As shown in FIG. 4, it can also set up so that an upper jaw orthogonal coordinate system may move to a lower jaw orthogonal coordinate system so that each coordinate axis performs the movement of the denture data 8 of the mandibular denture data 9 represented in the occlusion-state reproduction step.

(5) The determination step for grinding portion, which determines grinding data under static conditions or defined conditions from a portion surrounded by the image of upper and lower jaws from the reproduced occlusion state, will be described.

Here, the region surrounded by the 3D data set in the step of reproducing the occlusion state, that is, as shown in FIG. 4, the region where the occlusion surface of the artificial tooth of the upper jaw and the occlusion surface of the artificial tooth of the lower jaw are overlapped, is observed.

In the case where the region surrounded by the 3D-data is small, the dentures lack in stability. Thus, an overlapped portion of maxillomandibular 3D-data is adjusted by the hinge movement of maxillary 3D-data or movement thereof in the direction of lowering an occlusal vertical dimension. If the overlapped portion of the 3D-data is large, there is no cusp of the tooth due to a large number of cuttings. Thus, an overlapped portion of maxillomandibular 3D-data is adjusted by the hinge movement of maxillary 3D-data or movement thereof in the direction of increasing the occlusal vertical dimension. The hinge movement or the shift in occlusal vertical dimension may be used in arbitrarily combination.

Figure 5A:
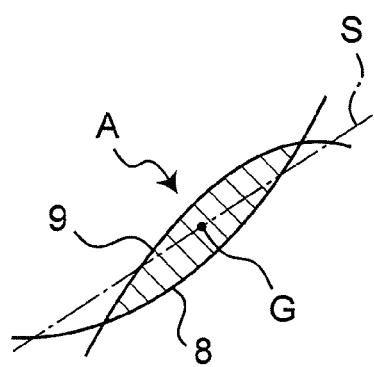
FIG. 5A is a diagram illustrating a portion surrounded by the three-dimensional data of the maxillomandibular occlusal surfaces.

Next, as illustrated in FIG. 5A, a grinding surface is determined by moving the maxillary 3D-data 8 or the mandibular 3D-data 9 so that the 3D-data overlapped portion A is frictionally moved during the movement of the upper and lower jaws. It is performed by cutting each 3D-data overlapped portion along the arbitrary defined grinding surface S at the time of forward movement, back movement, or lateral movement from the centric occlusal position.

Figure 5B:
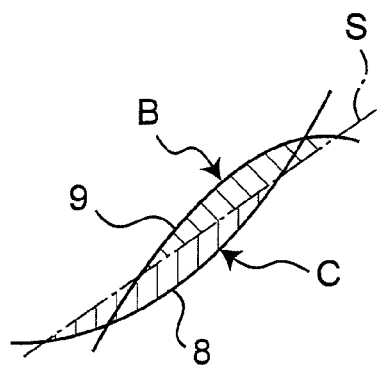
FIG. 5B is a diagram illustrating a grinding portion of the maxillomandibular occlusal surfaces.

Although the grinding surface S may not pass through the maxillomandibular 3D-data overlapped portion, preferably, it may pass through the overlapped portion between the maxillary 3D-data 8 and the mandibular 3D-data 9. As illustrated in FIG. 5B, cuspal portions B and C surrounded by the surface extended from the grinding surface S in the overlapped portion between 3D-data 8 and 9 are provided as cutting portions, respectively. These portions are referred to as grinding portions and the data thereof is referred to as grinding data.

The arbitrary defined grinding surface S is a surface extending in the direction of a forward movement, a backward movement, or a lateral movement and the angle of each surface is arbitrary defined with respect to an occlusal plane. It is preferable that the angle of the grinding surface S is set to 5 to 60 degrees with respect to the occlusal plane. An angle of a surface where the cusp of tooth touches is preferably 5 to 45 degrees in the forward or backward direction and 20 to 60 degrees in the lateral movement.

The movement direction is a direction along which the maxillary orthogonal coordinate system moves with respect to the mandibular orthogonal coordinate system at an arbitrary point within the range surrounded by the maxillary 3D-data and the mandibular 3D-data in the dynamic relation represented by the occlusion-state reproduction step. The movement direction is preferably linear. Alternatively, the movement direction may be curved. The movement direction may be approximate to a straight line. Alternatively, a curved line may be applied to the movement direction. In other words, the movement direction is a straight line or a curved surface. Preferably, it is a straight line or cylindrical surface.

Furthermore, the arbitrary point in range A surrounded by the maxillary 3D-data 8 and mandibular 3D-data 9 is the center of gravity G of the range surrounded by maxillary 3D-data 8 and the mandibular 3D-data 9.

When the range surrounded by the maxillary 3D-data 8 and the mandibular 3D-data 9 is represented by n points on the space, the center of gravity G is preferably calculated as X', Y', Z' obtained by converting X, Y, and Z axis of a mandibular orthogonal coordinate system and X, Y, and Z axis of a maxillary orthogonal coordinate system XYZ axis into those of the same orthogonal coordinate system, respectively, and dividing the sums of the values of the respective axes X, Y, and Z are divided by n. The grinding surface S is a plane including the movement direction of the upper jaw with respect to the lower jaw that passes through the values of X', Y', and Z'.

This movement direction is calculated by the reproduction method represented in the occlusion-state reproduction step. When the movement direction is reproduced by the articulator, these adjustment mechanisms can be reproduced on the computer in the case of an arcon type articulator or a condylar type articulator. The arcon type articulator is preferable.

The condylar distance of the articulator is 50 to 170 mm, preferably 80 to 140 mm, more preferably 100 to 120 mm. It is preferred to have an average condylar distance as a fixed value of 110 mm. A distance between the upper arch and the lower arch is about 80 to 120 mm. Any distance between the upper arch and the lower arch is allowable as long as it is determined where appropriate.

The condylar distance and the distance between the upper arch and the lower arch are calculated from numerical values previously defined by the condyle path regulatory mechanism and the incisal patch regulatory mechanism, which specify the maxillomandibular movement of the articulator.

Specifically, examples of the condyle path regulatory mechanism include an inclination of sagittal condylar path, a balancing-side lateral condyle path, a regulatory mechanism for immediate side-shift, and a regulatory mechanism for an angle of lateral condyle path on the working side. Examples of the incisal path regulatory mechanism include a sagittal incisal path inclination and a lateral incisal path guide angle.

An inclination of sagittal condylar path is −30 degrees to +90 degrees, preferably −0 degree to +50 degrees, more preferably −20 degrees to +80 degrees.

A balancing-side lateral condyle path is 0 degrees to +40 degrees, preferably +10 degrees to +20 degrees, more preferably 0 degree to +30 degrees.

A regulatory mechanism for immediate side-shift is 0 to 5 mm, preferably 0 to 8 mm, more preferably 0 to 10 mm.

A regulatory mechanism for an angle of lateral condyle path on the working side is −50 degrees to +60 degrees, preferably −40 degrees to +50 degrees, more preferably −30 degrees to +30 degrees.

A sagittal incisal path inclination is −30 degrees to +90 degrees, preferably −20 degrees to +80 degrees, more preferably −10 degrees to +75 degrees.

A lateral incisal path guide angle is −0 degree to +90 degrees, preferably −0 degrees to +50 degrees.

The maxillary orthogonal coordinate system is calculated with respect to the mandibular orthogonal coordinate system, which can move in accordance with these regulation mechanisms.

From the names or the like of commercial articulators, settings which can appropriately select only adjustment items are preferable. In the case where an unadjustable articulator is used, it is preferable that the fixed values of the articulator are fixedly entered without change when the name of this articulator is selected. The defined conditions are conditions being set to remove protruded portions to prevent upper and lower jaws from being caught while allowing them smoothly rubbing with each other.

The grinding data obtained in the present step is used as CAD data for grinding dentures. An NC program for processing in the grinding step for pre-grinding dentures is prepared. A computer numerical control (CNC), which controls a moving distance, a moving speed, and so on of tools in machine work by a computer, is used for grinding dentures. This process is referred to as CAM.

Figure 6:
FIG. 6 is a diagram illustrating a grinding portion of the occlusal surface.

FIG. 6 is a diagram illustrating faces to be ground in occlusal surfaces. Grinding is performed substantially in a bilaterally-symmetric manner. Thus, lead lines 1, 2, and 3 represent only one of jaws, respectively. When the upper and lower jaws are occluded, occlusal facets, where the upper and lower jaws make contact with each other, come into surface contact with the corresponding ones. Thus, the occlusal facets become surfaces being rubbed in accordance with the movement of the jaws.

Lead line 1 denotes posterior occlusal facets, lead line 2 denotes protrusive occlusal facets, and lead line 3 denotes balancing occlusal facets.

In other words, in the figure, reference numeral 1 denotes each of the surface portions to be ground at a certain angle, 2 denotes each of the surface portions to be ground at another angle, and 3 denotes the surface portions to be ground at a still another angle. However, these surfaces represented by these reference numerals are illustrative only. When considering occlusal static or dynamic relation, it is preferable to adjust or calculate the angles of the respective surfaces so that the surfaces are rubbed with the corresponding surfaces in their correct directions. Alternatively, however, these surface portions may be those to be ground almost at the same angle.

(6) The preparation step for denture data with reference points having grinding data, in which the denture data with reference points having grinding data, where denture data with reference points is additionally provided with grinding data, is prepared, will be described.

The grinding surface, which is the above grinding data, is aligned with the denture data with reference points to determine a grinding portion, thereby obtaining denture data reference points having grinding data. Here, based on the reference points, an important point is that a portion which should not be ground and a portion which should be ground are defined based on the reference points.

Therefore, by overlapping the indication parts of the reference points that represents a positional relationship between dentures and the reference point portions of the denture data with reference points having grinding data together, grinding portions of the dentures can be determined.

(7) A grinding step for pre-grinding dentures, which grinds a pre-grinding denture based on the denture data with reference points having grinding data, will be described.

Grinding data is used as CAD data and create an NC program for processing in this step. This is a program of a computer numerical control (CNC) which controls a moving distance, a moving speed, and so on tools in machine work by a computer. Grinding of dentures is performed using this program.

2. Program for Calculating Grinding Portion of Pre-Grinding Denture

It is preferable to perform each of the above steps by a series of programs.

Specifically, a dental program for calculating a grinding portion of a pre-grinding denture includes:

a data-input step of inputting a maxillomandibular jaw-relation reproduction condition and maxillomandibular denture data with reference points having reference points that define a positional relationship between the maxillomandibular jaw-relation reproduction condition and an upper jaw and a lower jaw;

an identification step for a position of maxillomandibular denture data, which determines a positional relationship between maxillary denture data and mandibular denture data by using the reference points with reference to the jaw-relation reproduction condition of input data;

a determination step for a grinding portion, which determines a range surrounded by maxillomandibular denture data to be prepared by using the jaw-relation reproduction condition and changing of occlusal vertical dimension; and a calculating step for grinding data, which determines grinding surfaces at an angle with respect to an occlusal surface determined by jaw-relation reproduction condition and input of an operator in the region surrounded by the maxillomandibular denture data obtained by the determination step for a grinding portion, and calculates grinding data surrounded by the grinding surfaces of maxillomandibular denture data.

Furthermore, the calculating step for grinding data may determine a grinding surface at an angle between an occlusal surface determined previously or by input of the operator and a movement direction found in a process for forming a region surrounded by maxillomandibular denture data under the jaw-relation reproduction condition in an arbitrary point in a region surrounded by maxillomandibular denture data obtained by the determination step for grinding portion, and calculates grinding data surrounded by the grinding surface of the maxillomandibular denture data.

The movement direction in the range surrounded by maxillomandibular denture data is a trajectory direction until an arbitrary point in a region surrounded by maxillomandibular denture data is disappeared from the generation of the region surrounded by the maxillomandibular denture data under maxillomandibular jaw-relation reproduction condition. When the present trace performs a complicated movement, the movement direction may be determined using an approximate value.

In addition to the dental program for calculating a grinding portion of a pre-grinding denture, based on the calculated grinding data, it is preferable to prepare a processing NC program is prepared and make it into a dental denture-grinding program having step of grinding dentures. It is also possible to configure a dental occlusal grinding apparatus, which uses grinding data, prepares a processing NC program, and performs denture grinding. By using a program of the present invention, grinding can be carried out easily even if an operator is not an experienced technician. The use of a CAM system allows the apparatus to carryout a grinding work. Thus, an operator is prevented from being injured with cutting scrap pieces and also prevented from breathing dust at the time of grinding. The worker can work without worrying about health.

The grinding of this invention is preferably performed using a diamond abrasive agent, and preferably ends finish with buffing polishing.

Since one or both of the maxillomandibular denture data with reference points are moved to change dynamic relation or occlusal vertical dimension, it is preferable to determine the final position of the maxillomandibular denture data by the number of ranges surrounded by the maxillomandibular denture data. The number of a range surrounded by the maxillomandibular denture data is 3 to 62 faces. Furthermore, it is preferably 9 to 62 faces.

More preferably, the number of protrusive occlusal facets is 1 or more for each of front tooth, left side, and right side, or 3 or more in total. The number of posterior occlusal facets is preferably 2 or more for each of the left and right sides, or 4 or more in total. The number of balancing occlusal facets is preferably 2 or more for each of the left and right sides, or 4 or more in total. Dentures can be prevented from being overturned due to chewing and deglutition.

As for such positional relationship, it is preferred to calculate the positional relationship of the range surrounded by maxillomandibular denture data according to the image recognition of the entire dentures. Alternatively, there is a method for roughly dividing the form of a denture into a front tooth part, a molar buccal cusp part, and occlusal surface part and calculating the numbers of contact portions in the respective parts. Furthermore, facets previously formed on the cusp of an artificial tooth may be calculated, and a protrusive occlusal facet, a posterior occlusal facet, a balancing occlusal facet may be then found from the angles of the respective facets to calculate the number of contact portions. Alternatively, these methods may be combined.

Furthermore, image data of artificial tooth occlusal surface may be set for a program. In this case, it is possible to find out the artificial tooth part from the resulting denture data to make it possible to grind any protrusive occlusal facet, posterior occlusal facet, and balancing occlusal facet. Thus, a maxillomandibular grinding portion can be exactly determined.

Furthermore, a final position can be determined by calculating the volume of the range surrounded by the maxillomandibular denture data. The program may be set to cause an error when the volume exceeds a predetermined level so that the grinding can be suspended to avoid a trouble of excess grinding.

An artificial tooth to be used for a denture grinding method is an artificial tooth for automatic grinding. A food-flowing groove of 0.5 to 3.0 mm in distance between a protrusive occlusal facet and a posterior occlusal facet is present between cusps of the adjacent artificial teeth. When cutting in a dental occlusal grinding apparatus, it is preferable to separate and prepare a protrusive occlusal facet and a posterior occlusal facet in advance to prevent their other portions from being accidentally cut at the time of cutting between the respective occlusal facets. A preferable distance between the protrusive occlusal facet and the posterior occlusal facet is in the range of 1.0 to 2.0 mm. By being separated from each other, abrasives can be prevented from accidentally deleting a different portion. The depth of the space between the protrusive occlusal facet and the posterior occlusal facet is in the range of 0.2 to 3.0 mm. The desirable depth is in the range of 0.5 to 1.5 mm.

3. Use of Grinding Method to Occlusal Adjustment Method

The above inventive grinding can be generally used in the inventive occlusal adjustment. Similarly, the inventive occlusal adjustment can be generally used in the inventive occlusal adjustment.

Furthermore, the inventive occlusal adjustment can be also used for prosthesis among dentures, particularly used for inlay prosthesis or onlay prosthesis. Preferably, it can be used for adjusting the occlusion state of filled prosthesis. A patient and a dentist can easily confirm whether the adjustment has been correctly performed. After time passes from a treatment, it can be used as a record of the situation of the past medical treatment. Thus, the justification of medical treatment can be easily determined.

The above (1) to (4) and (6) of the invention, which can be provided for grinding, may be used for an occlusal adjustment method in a similar manner.

However, the step of preparing a pre-grinding denture in the inventive technology (2) of the grinding is not a step for occlusal adjustment but a step of preparing a denture before occlusal adjustment. By reading grinding as an occlusal adjustment, the description of (2) may be provided as the description of the step of preparing a denture before occlusal adjustment.

(2) The production step for a pre-occlusal denture will be described. Here, dentures are produced and ground according to the jaw-relation reproduction conditions of the occlusion-state reproducing apparatus to produce pre-occlusal adjustment dentures before the step of occlusal adjustment.

The process for pre-occlusal adjustment denture production is a process for producing dentures according to the maxillomandibular relation obtained in the above process for occlusion-state reproduction. In other words, the process for pre-occlusal adjustment denture production is a process for producing a normal denture. In the typical process, a wax rim is formed and the artificial teeth are arranged along the wax rim. Then, a denture is prepared by a lost wax process and then subjected to grinding. Here, the production method is not particularly limited. The pre-grinding denture can be produced by any typical procedure.

Where dentures are only subjected to conventional grinding, correct occlusion suitable for a patient is hardly performed. In order to carry out correct occlusion suitable for the patient, the grinding of the occlusal surface is performed according to the present invention.

Occlusal adjustment data can be used for (6).

In the case of performing the occlusal adjustment method of the present invention, it is preferable to use 3D-data with natural teeth data where upper and lower jaws have natural teeth thereon rubbing against the corresponding natural teeth.

(6) A preparing step for denture data with reference points having occlusal adjustment data, where denture data with reference points is provided with occlusal adjustment data, will be described.

The occlusal adjustment surface, which is the above occlusal adjustment data, is aligned with denture data with reference points to determine an occlusal adjustment portion, thereby obtaining denture data with reference points having occlusal adjustment data. Here, an important point is that a portion which should not be subjected to occlusal adjustment and a portion which should be subjected to occlusal adjustment are defined based on the reference points.

Therefore, by overlapping indication parts of the reference points that represents a positional relationship between dentures and reference points portion of the denture data with reference points having occlusal adjustment data together, occlusal adjustment portions of the dentures can be determined.

(5) A determination step for occlusal adjustment portion, which determines occlusal adjustment data under static conditions or defined conditions from a portion surrounded by the image of upper and lower jaws from the reproduced occlusion state of (5), will be described.

The technology used in the determination step for grinding portion can be used.

Likewise, this technology also pays attention to the range surrounded by 3D-data matched in the process for occlusal state reproduction. However, in the case of occlusal adjustment, one jaw is natural teeth data. The natural teeth should not be subjected to grinding. Then, a grinding portion is decided to perform grinding only on the prosthesis data side.

Thus, in the occlusal adjustment method of the present invention, 3D-data having natural teeth data where upper and lower jaws have natural teeth thereon rubbing against the corresponding natural teeth is preferable.

In the case of 3D-data without rubbing natural teeth data, an occlusal adjustment portion is determined in a manner similar to one that creates grinding data based on the jaw-relation reproduction condition.

The rubbing natural teeth data means a data portion that keeps a state where it is not surrounded by the maxillomandibular data when each of maxillary data and mandibular data is considered as a single face.

4. In Case of Natural Teeth

A case where 3D-data is one having natural teeth data rubbing against each other in the upper and lower jaws will be described.

(A) Maxillomandibular 3D-data having at least one natural data portion rubbing each other in the upper and lower jaws is identified.

(B) The natural data portions rubbing each other in the upper and lower jaws are overlapped to identify the maxillomandibular 3D-data, thereby providing face data of rubbing natural teeth portion. The above term "rub" or "rubbing" preferably means "slide smoothly" or "sliding smoothly".

(C) An occlusal adjustment portion is determined by moving maxillomandibular 3D-data along with at least one face data of rubbing natural teeth portion and remaining a trace of a region surrounded by 3D-data on the side of prosthesis data to determine a region surrounded by the 3D-data as an occlusal adjustment portion.

The face data of rubbing natural teeth portion is preferably a plurality of face data of rubbing natural teeth portions which are not in the same plane. It is preferable that they are located at three or more different places. It is preferred that the face is one formed at the time of a forward movement, a back movement, or a lateral movement.

It is preferable that face data of rubbing natural teeth portion is positioned at a proximal side cusp and a distal side cusp with respect to prosthesis.

At the step of (B), the 3D-data is laid so that it can be rubbed with the natural teeth data portion. In this case, only a prosthesis portion is included in the range surrounded by the maxillomandibular 3D-data. As a point different from one at the grinding, the natural teeth are not subjected to grinding, the prosthesis serves as a portion where occlusal adjustment is performed. Thus, a prosthesis data portion intruded in the natural teeth 3D-data is subjected to occlusal adjustment.

The term "occlusal adjustment" means that a portion of an actual prosthesis corresponding to a portion represented on the data is ground.

Next, in order to determine an occlusal adjustment portion to be rubbed at the time of maxillomandibular movement, rubbing ranges of the respective upper and lower 3D data are set and the image portions thereof are rubbed against each other. Thus, a prosthesis 3D-data portion in the region surrounded by the natural teeth 3D-data is provided as an occlusal adjustment portion to be ground.

A method for determining face data of rubbing natural teeth portion of (B) is not specifically limited. However, for example, it may be one described below.

Rubbing natural teeth data portions of the upper and lower jaws are approximated to plane data, respectively.

Then, the planes of the rubbing natural teeth data portions of the upper and lower jaws are laid on each other so that their planes are matched as much as possible. At the most matched portion, the plane data of the corresponding rubbing natural teeth data portions of the upper and lower jaws are approximated and provided as plane data commonly included in the final rubbing natural teeth data portions of the upper and lower jaws. A rubbing natural teeth data portion is provided as the same data as that of the overlapped portion of the upper and lower jaws and approximated to a plane to provide such a plane as common plane data rubbing against the upper jaws.

5. Method for Representing Occlusal Adjustment Portion of Dental Prosthesis

Another invention will be described. This invention relates to a method for representing an occlusal adjustment portion of a dental prosthesis by using computer 3D-data, where the 3D-data includes prosthesis data and its corresponding natural teeth data containing rubbing natural teeth data in the upper and lower jaws.

This method includes the following steps:

(A) An identification step for a rubbing natural teeth data portion, where a rubbing natural teeth data portion in the upper and lower jaws is identified in maxillomandibular 3D-data. The rubbing portion may be the entire natural data. In addition, the occlusal surface portion of the prosthesis may be specified and all the other portions may be identified as rubbing portions.

(B) An identification step for slide movement of natural teeth portion face data, where it is identified so that rubbing natural teeth data portions in the upper and lower jaws are laid on each other and overlapped rubbing natural teeth data portions are slide smoothly.

Here, it is identified on a computer so that they are slid smoothly on a sliding surface.

(C) A determination step for an occlusal adjustment portion, where an occlusal adjustment portion is determined by moving maxillomandibular 3D-data along with at least one face data of rubbing natural teeth portion and remaining a trace of a region surrounded by 3D-data on the side of prosthesis data to determine a region surrounded by the 3D-data as an occlusal adjustment portion.

It is important to display the prosthesis data in which the trace of the region surrounded by 3D-data obtained by this method is remained.

6. Dental Program for Representing State of Contact Portions

A dental program for representing state of contact portions, which represents the state of contact portions between an upper jaw and a lower jaw, according to the present invention will be described.

The above inventive technologies of grinding and occlusal adjustment can be generally used in the inventive technology of the dental program for representing state of contact portions.

Similarly, the inventive technology of a dental program for representing state of a contact portion can be generally used in the inventive technologies of grinding and occlusal adjustment.

The dental program for representing state of contact portions, which represents the state of contact portions between an upper jaw and a lower jaw, is a program which is capable of confirming grinding, occlusal adjustment, and an arrangement state of artificial tooth. The program allows a dental student to easily confirm grinding, occlusal adjustment, and an arrangement state of artificial tooth. Furthermore, the program allows a dentist to employ the data as evidence for his or her appropriate work and to determine whether grinding, occlusal adjustment, and artificial tooth arrangement have been performed correctly. By providing an acceptable range, the program can be used in a common student examination and also used in a national wide common examination. The present invention allows a user to confirm maxillomandibular conditions by 3-D data and observe a maxillomandibular relation in a so-called skeleton state.

The term "skeleton state" means a state representing a three-dimensional (3D) figure by points and lines on a PC screen and allowing a user to almost grasp the configuration of the 3D figure and the configuration of another figure even if one is in front or back of the other. Preferably, these figures are wired to each other as they are represented by dashed lines.

The data input means which inputs mandibular data is to input the maxillomandibular 3D-data in a computer. The jaw data includes intraoral natural dental data, dental data containing prosthesis, and prosthesis data. The jaw data may be data of an occlusal surface where the upper and lower jaws are contact to each other.

The determination means for maxillomandibular data positions of reproducing a jaw relation of maxillomandibular data may be also used in the method of the invention.

The method for reproducing a jaw relation specifies a surface where the upper and lower jaws are brought into contact with each other as a specified surface. The number of the special surfaces is 3 to 62. More preferably, it is 9 to 62. A plane is calculated from the 3-D data of the specific surface. The calculation method to be used may be a least-squares method. A plane-setting position is calculated using the gravity center of the specific surface $((X)=\Sigma Xn/n$, $(Y)=\Sigma Yn/n$, $(Z)=\Sigma Zn/n)$ and the plane passing through the points is defined. It is possible to set the plane so that a least sum of the distances of the gravity centers of the respective maxillomandibular specific surfaces is obtained. The maxillomandibular specific surfaces are provided with the corresponding perpendicular lines. Angles formed by the perpendicular lines on the respective maxillomandibular specific surfaces are adjusted so that a sum of these angles becomes the minimum, while being set to obtain a least sum of the distances of the gravity centers of the respective maxillomandibular specific surfaces.

Display means for the state of a maxillomandibular data contact position, where a portion having a specific opposing jaw data in a specific approximate region is displayed on the maxillomandibular data, displays a region, where a positional relationship between upper jaw data and lower jaw data becomes clear, in a maxillary specific positional relationship from the maxillomandibular data. A method for displaying such a state may be one that changes the size of the range (such as area or volume), blink, color, or the like. A display range is determined by measuring a distance from one jaw data to the other jaw data of the upper and lower jaws and is set to the shortest distance from one jaw data to the other jaw data. The distances of the respective jaw data are measured. It is preferable to display one having preferably a distance of 0 to 100 µm, more preferably 0 to 50 µm, further preferably 0 to 20 µm. Depending on the distance, the jaw data may be preferably displayed in layers with different colors.

Data input means for inputting a maxillomandibular jaw-relation reproduction condition, and maxillomandibular denture data with reference points that represent the maxillomandibular jaw-relation reproduction condition and their respective positional relationships will be described as an exemplary data input means. The data input means for the jaw-relation reproduction condition may utilize the data input means that inputs maxillomandibular denture data with reference points. Inputting data unit of the above invention can be used.

Determination means for maxillomandibular data position, which determines a positional relationship between the upper jaw and the lower jaw by using reference points with reference to the jaw-relation reproduction condition of input data, will be described as an exemplary determination unit for maxillomandibular data position. These methods may be those described above.

7. Evaluation Method of Dental Care

Hereinafter, a method of using a dental program for representing state of contact portion for evaluation of dental care will be described.

In the method to be used for evaluation of dental care, it is preferable that the display calculated in the dental program for representing state of contact portion is a score or numerical data.

The score is preferably one that previously defines a specific portion where the upper and lower jaws are brought into contact with each other and judges an acceptance by determining whether the upper and lower jaws are in the state of being contact. It is preferable to divide teeth into the left molar tooth, the right molar tooth, front teeth (from central incisor to cuspid), and specify them as specific portions, followed by displaying the contact states of the respective portions as scores. Any specific site can be defined and used as a score representing the contact state. It is preferable to determine surfaces being touched at the time of a forward movement, a back movement, and a lateral movement as specific sites and to display the contact states thereof, respectively. The display method is preferably provided for displaying an area or volume, more preferably area.

For example, in the case of a representation for state of contact portions at the time of grinding, the surfaces where jaws are brought into contact with each other are provided as the respective scores and the number of recognized contact states is converted to the number of scores to determine an acceptance.

As a result, the program of the present invention is used when the number of contact portions which are most excellent in the surface being contact at the time of a left-side back movement. If the state of contact to the most excellent contact portion is n−m, it is preferable to display (n−m)/n or (n−m)/n×100%. It is preferable that these displays may be performed by a combination of a horizontal forward movement, a backward movement, and a lateral movement, or the display of the state of contact to the specific contact portion may be performed by a combination of an area and a volume.

In the case of occlusal adjustment, the specific portion at the time of grinding is calculated as a range of prosthesis and displays the result by a score or a numerical data.

The present invention can be used at the time of preparing a denture. It can use for the occlusal adjustment of a prosthesis. The completion degree of grinding or occlusal adjustment can be confirmed.

What is claimed is:
1. A method for grinding a denture in denture production, comprising:
 (1) a jaw-relation reproduction step of determining a jaw-relation reproduction condition by measuring a jaw movement of a patient, and reproducing a jaw state of the patient on an occlusion-state reproducing apparatus in accordance with the jaw-relation reproduction condition;
 (2) a pre-grinding denture production step of arranging dentures on the occlusion-state reproducing apparatus in accordance with the jaw-relation reproduction condition and preparing pre-grinding dentures;
 (3) a measurement step for denture data with reference points of measuring denture data with reference points which is three-dimensional image data containing reference points that represents a positional relationship between the jaw-relation reproduction condition and the dentures and an occlusal surface of the dentures;
 (4) an occlusion-state reproduction step of reproducing an occlusion state of the denture data with reference points by using the jaw-relation reproduction condition on a three-dimensional image;

(5) a grinding data determination step of determining grinding data of grinding portions under a dynamic condition or set condition from a portion surrounded by an image of upper and lower jaws on the three dimensional image in a reproduced occlusal state;

(6) a preparation step for denture data with reference points having grinding data for preparing denture data with reference points having grinding data, where the denture data with reference points is additionally provided with the grinding data; and (7) a grinding step for pre-grinding dentures, which grinds the pre-grinding denture based on the denture data with reference points having grinding data.

2. A dental program for calculating a grinding portion of a pre-grinding denture, wherein the program allows a computer to execute a data input step of inputting a maxillomandibular jaw-relation reproduction condition and denture data with reference points having reference points representing a positional relationship between the jaw-relation reproduction condition and an upper jaw and a lower jaw;

a determination step for a position of maxillomandibular denture data with reference points of reproducing an occlusion state of the input denture data with the reference points by using the jaw-relation reproduction condition on a three-dimensional image, and determining a positional relationship of the denture data with reference points of the upper and lower jaws;

a grinding portion determination step of determining a portion surrounded by an image of upper jaws and lower jaws on the three-dimensional image in a reproduced occlusion state; and a grinding data calculation step of calculating grinding data of a grinding portion under a dynamic condition or set condition from the portion surrounded by the image of the upper and lower jaws.

3. An occlusion-state reproducing apparatus used for a denture grinding method according to claim 1, comprising:

an articulator having an upper arch that corresponds to an upper jaw of a patient and a lower arch that corresponds to a lower arch of the patient; and reference points on the upper arches and the lower arches.

4. Reference points denture data measurement apparatus used for a denture grinding method according to claim 1.

5. A dental occlusal grinding apparatus for grinding a denture, wherein a processing NC program is created by using grinding data calculated by a dental program for calculating a grinding portion of a pre-grinding denture according to claim 2.

6. An artificial tooth for automatic grinding, used as a denture in a denture grinding method according to claim 1, wherein a food-flowing groove of 0.5 to 3.0 mm is provided between a protrusive occlusal facet and a posterior occlusal facet that are present between cusps of the adjacent artificial teeth.

7. A method for determining an occlusal adjustment portion of a dental prosthesis by using a computer 3-D data, where the 3D-data includes rubbing natural teeth data in upper and lower jaws, prosthesis data and the natural teeth data corresponding thereto, the method comprising:

(A) an identification step for rubbing natural teeth data portion in upper and lower jaws for identifying a rubbing natural teeth data portion in the upper and lower jaws in maxillomandibular 3D-data;

(B) an identification step for smooth sliding of natural teeth portion face data for identifying so that the rubbing natural teeth data portion in the upper and raw jaws and the prosthesis data are laid on each other and the prosthesis data is smoothly slid on the rubbing natural teeth data portion in the upper and raw jaws; and (C) a determination step for an occlusal adjustment portion of determining an occlusal adjustment portion by moving maxillomandibular 3D-data along with at least one face data of rubbing natural teeth portion and remaining a trace of a region surrounded by 3D-data on the side of prosthesis data to determine a region surrounded by the 3D-data as an occlusal adjustment portion.

8. A program for determining an occlusal adjustment portion of a dental prosthesis by using a computer 3-D data, where the 3D-data includes rubbing natural teeth data in upper and lower jaws, prosthesis data and the natural teeth data corresponding thereto, the program allowing a computer to execute:

(A) an identification step for rubbing natural teeth data portion in upper and lower jaws for identifying a rubbing natural teeth data portion in the upper and lower jaws in maxillomandibular 3D-data;

(B) an identification step for smooth sliding of natural teeth portion face data for identifying so that the rubbing natural teeth data portion in the upper and raw jaws and the prosthesis data are laid on each other and the prosthesis data is smoothly slid on the rubbing natural teeth data portion in the upper and raw jaws; and (C) a determination step for an occlusal adjustment portion of determining an occlusal adjustment portion by moving maxillomandibular 3D-data along with at least one face data of rubbing natural teeth portion and remaining a trace of a region surrounded by 3D-data on the side of prosthesis data to determine a region surrounded by the 3D-data as an occlusal adjustment portion.

9. A dental program for representing state of a contact portion, which represents the state of a contact portion between an upper jaw and a lower jaw, the program allowing a computer to execute:

a data input step of inputting maxillomandibular data;

a determination step for a position of maxillomandibular data position of reproducing an occlusal state of the maxillomandibular data and determining a position of the maxillomandibular data; and a display step for state of contact position of maxillomandibular data of displaying a portion having a specific opposing jaw data in a specific approximate region of the maxillomandibular data.

10. The dental program for representing state of a contact portion, which represents the state of a contact portion between an upper jaw and a lower jaw, according to claim 9, wherein the data input step is for inputting a maxillomandibular jaw-relation reproduction condition, and maxillomandibular denture data with reference points that represent a positional relation between the maxillomandibular jaw-relation reproduction condition and upper jaw and a lower jaw; and the determination step for the maxillomandibular data position is for determining a positional relationship between the upper jaw and the lower jaw by using reference points in accordance with the jaw-relation reproduction condition of input data.

* * * * *